US010589055B2

(12) United States Patent
Santostasi et al.

(10) Patent No.: US 10,589,055 B2
(45) Date of Patent: Mar. 17, 2020

(54) PHASE-LOCKED LOOP TO ENHANCE SLOW WAVE SLEEP

(71) Applicant: Northwestern University, Evanston, IL (US)

(72) Inventors: Giovanni Santostasi, Mount Horeb, WI (US); Phyllis Zee, Oak Park, IL (US)

(73) Assignee: Northwestern University, Evanston, IL (US)

( * ) Notice: Subject to any disclaimer, the term of this patent is extended or adjusted under 35 U.S.C. 154(b) by 243 days.

(21) Appl. No.: 15/517,458

(22) PCT Filed: Aug. 14, 2015

(86) PCT No.: PCT/US2015/045273
§ 371 (c)(1),
(2) Date: Apr. 6, 2017

(87) PCT Pub. No.: WO2016/028635
PCT Pub. Date: Feb. 25, 2016

(65) Prior Publication Data
US 2017/0304587 A1    Oct. 26, 2017

Related U.S. Application Data

(60) Provisional application No. 62/038,700, filed on Aug. 18, 2014.

(51) Int. Cl.
*A61M 21/02* (2006.01)
*A61M 21/00* (2006.01)
(Continued)

(52) U.S. Cl.
CPC ......... *A61M 21/02* (2013.01); *A61B 5/04012* (2013.01); *A61B 5/0482* (2013.01);
(Continued)

(58) Field of Classification Search
CPC ............................................. A61M 21/00–02
See application file for complete search history.

(56) References Cited

U.S. PATENT DOCUMENTS 5,241,967 A * 9/1993 Yasushi .............. A61B 5/04842
600/27
2008/0081941 A1   4/2008 Tononi
2016/0082222 A1* 3/2016 Garcia Molina .... A61B 5/0482
600/27

FOREIGN PATENT DOCUMENTS

WO      2014118650      8/2014
WO      2016028635      2/2016

OTHER PUBLICATIONS

European Patent Office, "Communication pursuant to Article 94(3) EPC," issued in connection with European Patent Application No. 15756288.5, dated Jun. 27, 2018, 5 pages.

(Continued)

*Primary Examiner* — Thaddeus B Cox
(74) *Attorney, Agent, or Firm* — Quarles & Brady LLP; Jonathan Stone

(57) ABSTRACT

Certain examples provide systems and methods to enhance slow wave sleep. An example method includes identifying a sleep stage for slow wave sleep in a subject being monitored. The example method also includes generating, following identification of slow wave sleep and using a processor including a phase locked loop, an output signal based on a phase of a reference input signal, the output signal phase locked according to the reference input signal. The example method includes delivering, during slow wave sleep for the subject, a stimulus to the subject based on the phase locked output signal. The delivering includes providing the stimulus in a series of signal pulses for a first period of time; and providing a refractory period without pulses in a second period of time. The method further includes measuring feedback from the stimulus.

22 Claims, 5 Drawing Sheets

(51) Int. Cl.
  *A61B 5/0484* (2006.01)
  *A61B 5/00* (2006.01)
  *A61B 5/04* (2006.01)
  *A61B 5/0482* (2006.01)

(52) U.S. Cl.
  CPC ........ *A61B 5/04845* (2013.01); *A61B 5/4812* (2013.01); *A61B 5/4836* (2013.01); *A61B 5/4857* (2013.01); *A61B 5/7242* (2013.01); *A61M 21/00* (2013.01); *A61B 5/7235* (2013.01); *A61M 2021/0027* (2013.01); *A61M 2230/10* (2013.01)

(56) References Cited

OTHER PUBLICATIONS

Pei-Chen Lo et al., "Applicability of phase-locked loop to tracking the rhythmic activity in EEGS," vol. 19, No. 3, May 1, 2000, 16 pages.

International Searching Authority, "International Search Report and Written Opinion", issued in connection with PCT patent application No. PCT/US2015/045273, dated Oct. 26, 2015, 12 pages.

International Searching Authority, "International Preliminary Report on Patentability", issued in connection with PCT patent application No. PCT/US2015/045273, dated Mar. 2, 2017, 8 pages.

Ngo et al., "Auditory Closed-Loop Stimulation of the Sleep Slow Oscillation Enhances Memory", Neuron 78, 545-553, May 8, 2013, 9 pages.

Oudiette et al., "Reinforcing Rhythms in the Sleeping Brain with a Computerized Metronome", Neuron 78, May 8, 2013, 3 pages.

Campbell et al., "Human and Automatic Validation of a Phase Locked Loop Spindle Detection System" Electroencephalography and Clinical Neurophysiology, Elsevier, vol. 48, No. 5, May 1, 1980 (May 1, 1980) pp. 602-605, 4 pages.

Broughton R et al: "A phase locked loop device for automatic detection of sleep spindles and stage 2", Electroencephalography and Clinical Neurophysiology, Elsevier, vol. 44, No. 5, May 1, 1978 (May 1, 1978), 4 pages.

Riedner et al, "Enhancing slow waves using acoustic stimuli", 2012 Society for Neuroscience Annual Meeting on Oct. 17, 2012, 1 page.

* cited by examiner

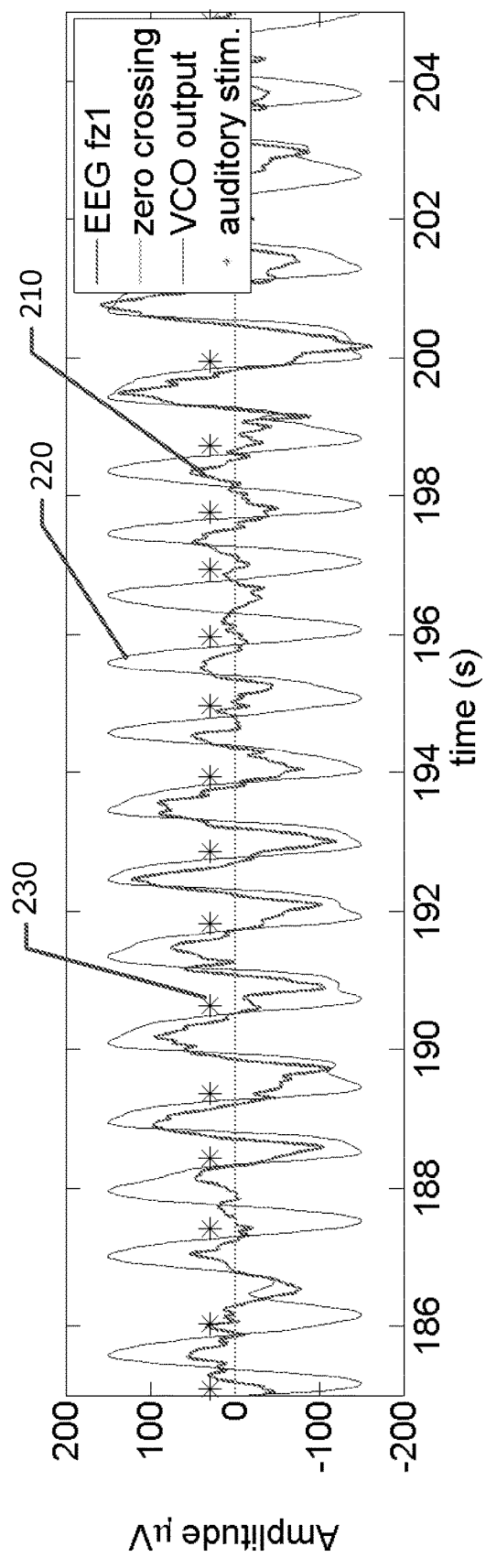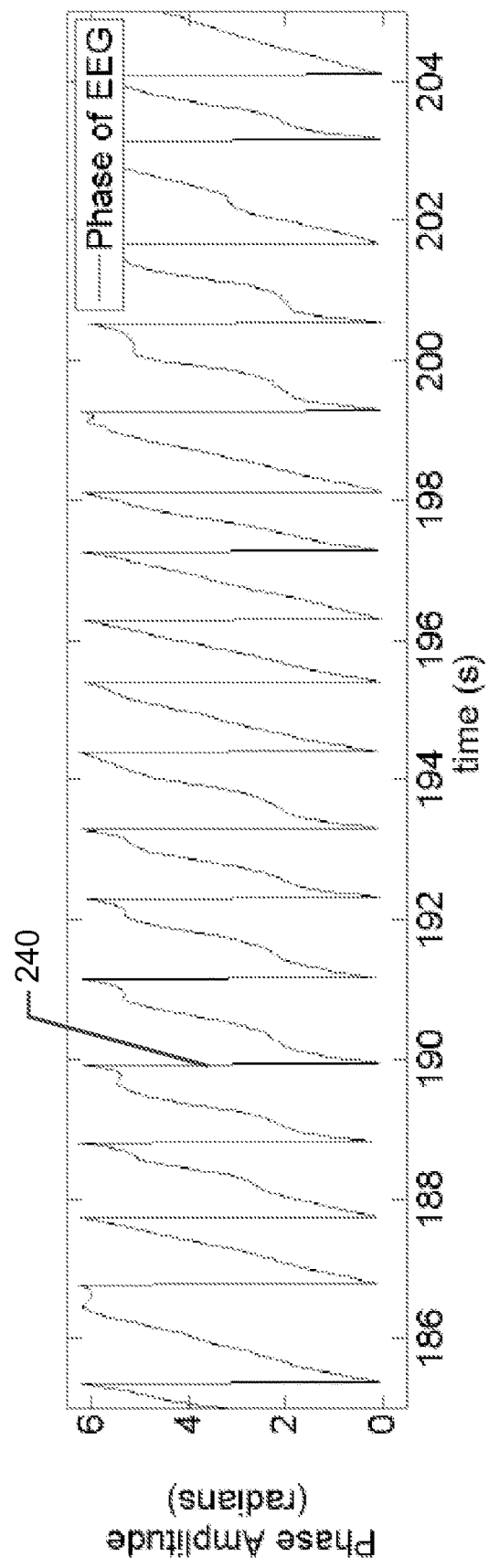
FIG. 2A
FIG. 2B

PHASE-LOCKED LOOP TO ENHANCE SLOW WAVE SLEEP

CROSS-REFERENCE TO RELATED APPLICATION

This patent arises from the U.S. national stage of International Patent Application Serial No. PCT/US2015/045273, having an International filing date of Aug. 14, 2015, and claims benefit of U.S. Provisional Application No. 62/038,700, entitled "PHASE-LOCKED LOOP TO ENHANCE SLOW WAVE SLEEP", filed on Aug. 18, 2014, which is hereby incorporated by reference in its entirety for all purposes.

STATEMENT REGARDING FEDERALLY SPONSORED RESEARCH OR DEVELOPMENT

[Not Applicable]

FIELD OF THE DISCLOSURE

This disclosure relates generally to sleep enhancement and, more particularly, to delivery of a stimulus at a particular phase of an electrophysiological rhythm to enhance brain electrical activity sleep.

BACKGROUND

The statements in this section merely provide background information related to the disclosure and may not constitute prior art.

Sleep is essential for a person's health and well-being according to the National Sleep Foundation. Millions of people, however, get insufficient sleep and even suffer from sleep deprivation. Lack of sleep can negatively impact a person's health, mental state, and general disposition. For example, a sleep-deprived person may experience slowed speech, altered emotional response, memory impairment, etc., and have trouble being creative. Lack of sleep can impact a variety of physiological systems including brain and nervous system, cardiovascular system, metabolic function, and immune system.

Sleep is prompted by natural cycles of activity in a brain and includes two basic states: rapid eye movement (REM) sleep and non-rapid eye movement (NREM) sleep. During sleep, a body cycles between non-REM and REM sleep. Typically, people begin the sleep cycle with a period of non-REM sleep followed by a short period of REM sleep.

The period of NREM sleep includes four stages. A completed cycle of sleep includes a progression through the four stages before REM sleep is attained, and the cycle repeats.

In stage 1 (N1) of NREM sleep, readings show a reduction in activity between wakefulness and stage 1 sleep. Stage 2 (N2) is a period of light sleep during which readings show intermittent peaks and valleys, or positive and negative waves. These waves indicate spontaneous periods of muscle tone mixed with periods of muscle relaxation. Stages 3 (N3) and 4 (N4) are deep sleep stages, with stage 4 being more intense than stage 3. Stages 3 and 4 are also referred to as slow-wave, or delta, sleep.

Slow-wave sleep (SWS) is a distinctive feature of sleep in and mammals. It has been shown that SWS has a restorative role, both mentally and physically, and is also associated with the stabilization of memories for long-term storage. Using memory consolidation occurring during SWS, as the brain transfers memories to long-term storage. Slow-wave sleep and slow wave activity diminishes with age, both in duration and intensity, and this decline correlates with impairments in cognitive performance and in particular memory retrieval.

In support of this observation, when compared to age-matched controls, individuals with mild cognitive impairment (MCI) have reduced slow-wave activity. In addition to cognition, slow-wave sleep appears to play an important role in the regulation of cardiometabolic function. Experimental suppression of SWS has been shown to impair metabolic function. Thus, enhancing slow-wave activity could have many beneficial ramifications.

BRIEF DESCRIPTION OF THE DRAWINGS

FIGS. 2A-2B show example input, output, and phase detector traces using the phase-lock loop circuit of FIG. 1.

Figure 1:
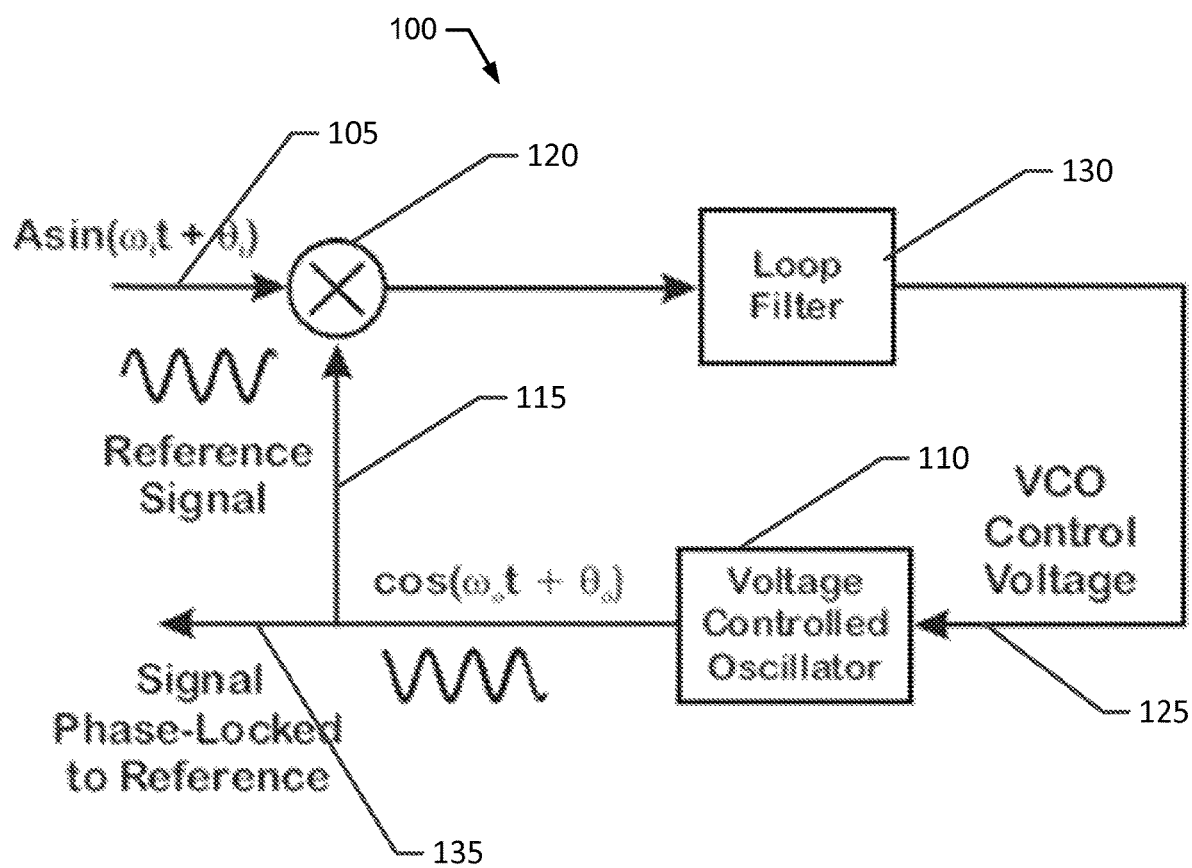
FIG. 1 illustrates an example phase-lock loop circuit.

The following detailed description of certain embodiments of the present invention will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

In the following detailed description, reference is made to the accompanying drawings that form a part hereof, and in which are shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe example implementations and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Certain examples provide systems, methods, apparatus, and the like, to enhance brain activity. In particular, certain examples provide a Brain Computer Interface (BCI) to enhance brain electrical activity during sleep. Certain examples exploit rhythmic activity typical of non-REM sleep to excite resonances through periodic acoustic stimulation.

In certain examples, a system to deliver a stimulus at a particular phase of an electrophysiological rhythm can be implemented using a Phase-Locked Loop (PLL). Using a PLL to deliver a stimulus to a subject's brain at a particular phase of its electrophysiological rhythm can enhance sleep quality and associated daytime neurocognitive performance, for example.

Slow wave sleep can be enhanced using transcranial Direct Current (tsDC), but locking is not possible using this technology because an electro-encephalogram (EEG) cannot be read during tsDC stimulation. Additionally, audio stimulation is safer and less invasive than tsDC. The Phase Locked Loop is a very efficient way to synchronize two clocks, and certain examples use the brain's own rhythm to increase synchronization between the firing of neurons during slow wave sleep to provide a unique approach to brain stimulation.

Certain examples affect an EEG by producing K-complex waves during lighter stages of NREM sleep. Such waves are similar to slow waves of deep sleep but are more parietal and can come in individual bursts. A K-complex is an EEG waveform that occurs during NREM sleep. A K-complex wave is characterized by a high amplitude slow wave that occurs with sleep spindles (e.g., in stage N2 sleep) as part of the EEG. A sleep spindle (sometimes referred to as a spindle, sigma band, or sigma wave) is a burst of oscillatory brain activity that occurs during stage N2 sleep. Spindles and K-complexes indicate the onset of stage N2 sleep and help define characteristics of stage N2 sleep.

While K-complexes include greater peaks and valleys, sleep spindles represent a series of dense waves with less variation in amplitude. Sleep spindles may help to block out external noises, resulting in a sounder sleep.

K-complex waves are more frequent in the first sleep cycles. K-complexes have two proposed functions. First, K-complexes are believed to suppress cortical arousal in response to stimuli that the sleeping brain evaluates not to signal danger. Second, K-complexes aid in sleep-based memory consolidation.

K-complexes are outward dendritic currents that are generated in the cerebral cortex. The outward dendritic currents are accompanied by a decrease in broadband EEG power including gamma wave activity. The decrease in broadband EEG power produces "down-states" of neuronal silence in which neural network activity is reduced. The activity of K-complexes is transferred to the thalamus where it synchronizes the thalamocortical network during sleep, producing sleep oscillations such as spindles and delta waves. The produced sleep oscillations are similar to identical in "laminar distributions of transmembrane currents" to the slow waves of slow wave sleep.

Auditory tones can affect the EEG by producing K-complex waves during lighter stages of NREM sleep. K-complex waves produced during lighter stages of NREM sleep are similar to slow waves of deep sleep (besides being more parietal and coming in individual burst).

Certain examples provide improved acoustic stimulation during sleep to provide a variety of benefits including enhanced deep sleep (e.g., SWA), improved sleep quality, improved memory, treatment of cognitive decline, etc.

II. Brief Description

Certain examples provide a method including identifying a sleep stage for slow wave sleep in a subject being monitored. The example method also includes generating, following identification of slow wave sleep and using a processor including a phase locked loop, an output signal based on a phase of a reference input signal, the output signal phase locked according to the reference input signal. The example method includes delivering, during slow wave sleep for the subject, a stimulus to the subject based on the phase locked output signal. The delivering includes providing the stimulus in a series of signal pulses for a first period of time; and providing a refractory period without pulses in a second period of time. The method further includes measuring feedback from the stimulus.

Certain examples provide a tangible machine readable medium having instructions stored thereon, which when executed, cause a machine to implement a method. The example method includes method including identifying a sleep stage for slow wave sleep in a subject being monitored. The example method also includes generating, following identification of slow wave sleep and using a processor including a phase locked loop, an output signal based on a phase of a reference input signal, the output signal phase locked according to the reference input signal. The example method includes delivering, during slow wave sleep for the subject, a stimulus to the subject based on the phase locked output signal. The delivering includes providing the stimulus in a series of signal pulses for a first period of time; and providing a refractory period without pulses in a second period of time. The method further includes measuring feedback from the stimulus.

Certain examples provide a system including a memory and processor including a phase lock loop. The memory stores instruction which, when executed by the processor, cause the processor to identify a sleep stage for slow wave sleep in a subject being monitored. The example instructions also cause the processor to generate, following identification of slow wave sleep, an output signal based on a phase of a reference input signal, the output signal phase locked according to the reference input signal. The example instructions also cause the processor to deliver, during slow wave sleep for the subject, a stimulus to the subject based on the phase locked output signal. The example delivering includes provide the stimulus in a series of signal pulses for a first period of time; and provide a refractory period without pulses in a second period of time. The example instructions also cause the processor to measure feedback from the stimulus.

III. Example Slow Wave Sleep Enhancement

Certain examples facilitate induction of slow waves with high amplitude to increase overall slow wave activity. Certain examples increase slow wave activity without producing additional arousals to supplement the arousals that occur naturally in a subject (e.g., a human subject).

Certain examples provide systems and methods for EEG phase-tracking using an adaptive feedback algorithm to deliver tones at a particular phase. Certain examples use a phase-locked loop (PLL), also referred to as a phase lock loop, which is a control system that generates an output signal at a phase systematically related to a phase of an input "reference" signal. When the PLL is implemented as an electronic circuit, the PLL includes a variable frequency oscillator and a phase detector. The circuit compares the phase of the input signal with the phase of the signal derived from its output oscillator and adjusts the frequency of its oscillator to keep the phases matched. The signal from the phase detector is used to control the oscillator in a feedback loop. In certain examples, an adaptive feedback algorithm based on a PLL that tracks the phase of an underlying EEG and delivers tones at a particular preferential phase can be adapted to any particular target phase and can adapt automatically to individual slow wave characteristics, while providing improved accuracy and precision with respect to target phase than other techniques.

Acoustic stimulation methods may be able to enhance slow-wave sleep without risks inherent in electrical stimulation or pharmacological methods. PLL methods differ from other acoustic stimulation methods that are based on detecting a single slow wave rather than modeling slow-wave activity over an extended period of time.

By providing real-time estimates and/or measurements of a phase of ongoing EEG oscillations/rhythms, the PLL can rapidly adjust to physiological changes, thus opening up new possibilities to study brain dynamics during sleep. Using a PLL can help enhance sleep quality and associated daytime behavior.

In certain examples, the PLL takes two input signals, one generated by a local oscillator and another derived from an external source, such as a broadcast carrier, and synchronizes waveforms of the two signals. By continuously (or substantially continuously given a periodicity and/or system latency) monitoring a phase of the external source signal and adjusting a phase of the local oscillator to match the phase of the external source signal, the PLL permits the external signal to entrain (e.g., modify the phase and/or period of) the local oscillator.

For example, the PLL circuit compares a phase of the input signal with a phase of a signal derived from the variable frequency output oscillator and adjusts a frequency of the oscillator to keep the phases matched. A signal from the phase detector is used to control the oscillator in a feedback loop.

In certain examples, PLL design is based on a ratio of phase in versus phase error. The ratio is calculated from parameters of individual components of the PLL and can be also measured from experimental data. In certain examples, the calculation of the radio also depends on a type of application of the PLL.

In certain examples, the PLL is used to synchronize two clocks or periodic processes (e.g., a reference process and a driver). The PLL is configured to stimulate slow-wave sleep activity by rhythmically generating an acoustic tone in a given range around a target frequency (e.g., 1 Hz) and also to phase lock with endogenous slow-wave oscillations of a subject's brain and deliver a stimulus signal to the brain at a particular phase. By synchronizing the stimulation with the phase of the EEG, efficacy and characteristics of slow-wave induction can be increased. In certain examples, signals from two clocks are multiplied and the PLL is filtered to produce a quantity proportional to the difference in phase that is then used to correct the driver clock to, as closely as possible, match a reference clock phase.

A PLL can be used to deliver an acoustic stimulus at a particular phase of an electrophysiological rhythm. Certain examples provide a slow wave stimulation method using a PLL by selecting a frequency of PLL (e.g., 1 Hz). A target phase is also selected at which to deliver a first tone to a subject. When the phase of the PLL is within a given range around the target phase, the first tone is played. However, if the phase of the PLL changes rapidly such that it exceeds the target phase before registering in the range of values, then a second tone is played. During "off" intervals, a "sham tone" is recorded as a fake or placeholder tone and its timing is stored but no sound is played.

Certain examples implement a PLL in an adaptive slow wave induction algorithm to achieve phase lock (e.g., pulses occur at a given value of the phase) in a dynamic, individual, and adaptive way. Using the PLL, resonances can be automatically identified to increase an amplitude of slow wave activity (SWA) through resonance. Delays between detection of phase and stimulus application can be compensated automatically by the PLL.

In an example, a stimulus is provided and resulting data is gathered from a subject via an automatic brain computer interface (BCI). In the example, data is recorded using an amplifier, such as a Brain Products V-Amp amplifier at a 500 Hz sampling frequency. Filtering can be applied (e.g., low-pass hardware filtering with cutoff frequency of 0.3 Hz) to an output of the amplifier. In the example, multiple channels can be used for monitoring and detection. A first channel is dedicated to detection of slow waves (e.g., anterior frontal channel Fpz referred to as a right mastoid reference) and two channels for differential electro-olfactogram (EOG). Electrodes (e.g., self-adhesive disposable electrodes such as Ag/AgCl electrodes) are placed on a subject to gather data via the plurality of channels. Data is then gathered and stored at a computer and/or other processor with memory via the electrodes. The data can be downsampled (e.g., with a downsampled frequency of 100 Hz) for storage. A program (e.g., a Matlab™ program) can be used to control acoustic stimulation for the BCI, and the subject wears headphones (e.g., Acoustic Sheep Sleep Phones SP4BM) to receive the audio stimulus.

In the example, an automatic protocol is provided to automatically categorize stages of sleep. The protocol measures a relative average power in different electro-encephalogram (EEG) frequency bands. In order to emphasize robustness in detecting N3 sleep, a simplified classification of sleep stages can be used. The automatic protocol starts with a default Wake stage until a Sleep stage is detected, at which point an algorithm is engaged to detect slow wave sleep. Stimulation begins once the slow wave sleep is detected.

For example, the following algorithm can be used to detect onset of slow wave sleep. First, a delta (e.g., 0.3-4 Hz) root mean square (RMS) continuous calculation is performed based on a certain measured period (e.g., the last 5 minutes) of recorded EEG activity to determine when a general Sleep stage occurs. The general Sleep stage roughly corresponds with early N2 stage of sleep. The Sleep stage is reached when the delta RMS is above an empirically determined threshold (e.g., the delta RMS threshold) for at least a certain period of time (e.g., 75 seconds). The delta RMS threshold is found by collecting data from a baseline night of sleep, calculating a histogram of the delta RMS, and taking a certain percentile value (e.g., a $40^{th}$ percentile value).

Alternatively or in addition, another criterion to determine when the sleep state is reached is a presence of spindles and a total spindle duration of a certain duration (e.g., 1.5 seconds in the last 30 seconds) combined with a delta RMS value equal to a certain percentage (e.g., at least 80%) of the delta RMS threshold, for example.

When the subject is in the sleep state, a K complex/slow-wave detection algorithm is executed. If a K complex is detected, brief auditory tones are played with a certain inter trial interval (ITI) (e.g., 5 seconds). For example, a stimulus pulses at a certain frequency or set of frequencies (e.g., a 50-ms sine-Gaussian pulse stimulus at 500 Hz with variation on this frequency to avoid habituation). The volume is adjusted and is increased by a small step if a K-complex response is detected in a short interval (e.g., approximately 2 seconds) after a stimulus and decreased if an increase in alpha or beta waves is observed (e.g., a response indicative of a possible arousal). Using this procedure, individualized auditory thresholds can be determined during sleep to be used in a slow wave stimulation protocol. A last setting of the volume achieved in the N2 stage can be used as a maximum volume in the N3 stage.

Once an onset of the N3 stage of sleep is detected, slow wave stimulation provides pulses with a certain ITI (e.g., approximately 1 second). A value of the ITI is adjusted according to a phase of the slow-wave EEG through application of a PLL. Tones are delivered when the phase of the EEG reaches a certain predetermined value. This phase value can be changed in process via a graphical user interface (GUI), for example. The stimulation procedure follows an alternating pattern of blocks of n tones that are played recorded (Block On) and n sham tones for which times are recorded but the tones are not played (Block Off). A number of tones is also a parameter that a user can change during the stimulation via the GUI.

In an example, a phase corresponding to a negative half-wave (e.g., just before the peak) and a sequence of n=5 tones is used. The example stimulation continues for each sleep cycle during N3 unless an arousal is detected (e.g., indicated by a sudden increase of beta or alpha). Following arousal detection, a refractory time with no stimulation (e.g., 30 seconds) is provided.

Thus, the PLL models a slow-wave EEG and can be used to create a pace maker to deliver stimuli at a particular phase of the slow wave. The slow-wave phase corresponds to different physiological states and neural activity such that acting at different phases can produce different effects. Even though slow waves tend to be a narrow-band phenomenon (e.g., from 0.3 to 4 Hz), the slow waves appear during regular sleep as short bursts of activity. The PLL oscillates in a regular manner between the bursts, and the PLL is able to follow non-linear behavior of slow waves during the bursts.

FIG. 1 illustrates a schematic representative of an example PLL circuit 100. The PLL circuit 100 is a control system that generates an output signal at a phase systematically related to a phase of an input reference signal. The PLL 100 can be used to recover a signal from a noisy communication channel, generate stable frequencies at a multiple of an input frequency, or distribute clock timing pulses in digital logic designs such as microprocessors. The PLL can also be implemented in hardware, software, and/or firmware. In certain examples, the PLL 100 implements a method of EEG phase-tracking including an adaptive feedback algorithm to deliver tones in a particular phase.

In certain examples, the PLL 100 can be implemented as an electronic circuit 100 including a variable frequency oscillator 110 and a phase detector 120. The PLL circuit 100 compares a phase of an input signal 105 with a phase of a reference signal 115 derived from its output oscillator 110 and adjusts the frequency of its oscillator 110 to keep signal phases matched. The signal from the phase detector 120 is used to control the oscillator 110 in a feedback loop including a filter 130 providing a voltage control signal 125 to the oscillator 110, for example. An output of the voltage controlled oscillator 110 provides the reference signal 115 as well as a signal 135 that is phase-locked to the reference signal 115.

Because frequency is a time derivative of phase, keeping input and output phase in lock step with the PLL 100 correlates with keeping input and output frequencies in lock step. Consequently, the phase-locked loop 100 can track an input frequency, or the PLL circuit 100 can generate a frequency that is a multiple of the input frequency. Tracking the input frequency can be used for demodulation, and generating a multiple of the input frequency can be used for indirect frequency synthesis, for example.

In certain examples the PLL 100 can analyze an EEG input and classify in real time (or substantially real time) an input frequency into a frequency range: alpha, beta, delta, or theta. The PLL 100 can also detect particular features of the EEG such as spindles.

In certain examples, the PLL 100 can be configured to rhythmically deliver an acoustic tone 135 via a brain computer interface (e.g., electrodes, headphones, etc.) in a given range around a target frequency and phase-locked with endogenous slow-wave oscillations. By synchronizing stimulation with the phase of the EEG, slow-wave induction is improved to deliver increased slow wave activity. In certain examples, the PLL 100 output 135 provides a flexible but limited range of frequencies that is phase-locked with the quasi-periodic fluctuations of the EEG during slow wave sleep.

The PLL 100 is an efficient tool for modeling EEG slow waves and can be used as a pacemaker to deliver stimuli at a particular slow-wave phase. Because slow-wave phase corresponds to different physiological states that directly influence neural activity, stimulation at different phases can produce different effects. Although slow waves tend to occur in a narrow band (e.g., from 0.5 to 4 Hz), during sleep, slow waves appear as short bursts of activity. The PLL 100 oscillates in a regular manner between bursts and is able to follow the non-linear behavior of slow waves during bursts. How well the PLL 100 can follow the EEG depends on parameter values, which can be adjusted to improve the performance of the PLL 100.

As shown in the example of FIG. 1, the PLL 100 includes the phase detector (PD) 120, the loop filter (LF) 130, and the voltage controlled oscillator (VCO) 110 operating on an input signal 105 to provide a reference 115 and phase-locked output 135.

In operation, let $s_1(t)$ be the input reference signal 105 (e.g., the EEG signal during slow-wave sleep). In certain examples, the signal 105 is assumed to be a sine wave with a given angular frequency $\omega$ (although an EEG can be a more complicated narrow band signal). The signal 105 also has a non-zero phase $\phi_1(t)$. Let $s_2(t)$ be another signal, also a sinusoidal function with angular frequency $\omega$, that is to be phase locked with the reference signal. This phase-locked signal 135 is used for auditory stimulation. The signal $s_2(t)$ has an initial phase difference with $s_1(t)$ equal to 90°. Multiplying the two signals provides:

$$s_1 = A_1 \sin[\omega t + \phi_1(t)], \qquad (\text{Eq. 1})$$

$$s_2 = A_2 \sin[\omega t + \phi_2(t)], \qquad (\text{Eq. 2})$$

$$s_3(t) = s_1(t) s_2(t) = K_d A_1 \sin[\omega t + \phi_1(t)] A_2 \sin[\omega t + \phi_2(t)], \qquad (\text{Eq. 3})$$

where $K_d$ is a gain of the multiplier or phase detector, $A_1$ and $A_2$ are amplifier gains. Equation 3 can be re-written using trigonometric identities:

$$s_3(t) = \frac{K_d A_1 A_2}{2} \sin[\phi_2(t) - \phi_1(t)] + \frac{K_d A_1 A_2}{2} \sin[2\omega t + \phi_2(t) + \phi_1(t)]. \qquad (\text{Eq. 4})$$

When rewritten as in Equation 4, the equation $s_3(t)$ has two distinct parts: a part that is frequency independent and a part that is a function of twice the original frequency (plus a sum of the two phases). The frequency-independent phase is a function of the phase difference $\phi_2(t)-\phi_1(t)$. Applying a low-pass filter to the multiplier $s_3(t)$ obtains an error signal:

$$s_e = \frac{K_{LPF}K_dA_1A_2}{2}\sin[\varphi_2(t)-\varphi_1(t)], \quad \text{(Eq. 5)}$$

where $K_{LPF}$ represents a low pass filter gain.

A last component of the PLL is the VCO 110. The error signal provides information about the input signal 105. To synchronize the output signal with input signal, the error signal is reduced or minimized by changing the phase of signal $s_2(t)$ to match the phase of signal $s_1(t)$. The VCO 110 generates a periodic signal with a frequency that is proportional to a control signal, such as the error signal. When the error signal is zero, the VCO 110 in the PLL 100 produces a signal 135 with a center frequency that is equal to the input signal 105. When the error signal is non-zero, the VCO 110 responds by changing its frequency. A rate of change of the frequency in the VCO 110 represents a sensitivity or gain, $K_o$, of the VCO 110:

$$K_o = \frac{d\omega_i}{dv}, \text{ or} \quad \text{(Eq. 6)}$$

$$\omega_{out} = \omega_c + K_o s_e(t) = \omega_c + \phi_2(t). \quad \text{(Eq. 7)}$$

As shown in the example of FIG. 1, the PLL 100 includes the phase detector (PD) 120, the loop filter (LF) 130, and the voltage controlled oscillator (VCO) 110 operating on an input signal 105 to provide a reference 115 and phase-locked output 135. The phase is an integral of the frequency:

$$\phi_i = 2\pi\int_0^t f_i(t)dt, \quad \text{(Eq. 8)}$$

and substituting for $K_o$:

$$\phi_2(t) = 2\pi K_o\int_0^t s_e(t)dt = 2\pi K_o s_e(t)t, \quad \text{(Eq. 9)}$$

under an assumption of a linear error.

Then, if the error signal has a non-zero amplitude, the phase of the VCO signal continues to increase until it goes back to zero. The error signal can be rewritten as:

$$s_e(t) = \frac{K_{LPF}K_dA_1A_2}{2}\sin[2\pi K_o s_e(t)t - \varphi_1 t], \quad \text{(Eq. 10)}$$

where $\phi$ represents a function and $\varphi$ represents a phase in an argument of a sine function.

Assuming that the error in phase is small, then Equation 9 can be simplified using $\sin(\theta)\approx\theta$:

$$s_e(t) = \frac{K_{LPF}K_dA_1A_2}{2}[2\pi K_o s_e(t)t - \varphi_1 t]. \quad \text{(Eq. 11)}$$

If the error signal is non-zero, then the phase continues changing linearly. However, as the phase of the VCO changes, the updated difference in phase becomes smaller at the next iteration. This process continues until the error signal amplitude approaches zero.

In certain examples, the PLL 100 behaves like a band-pass filter but with a smoother response and a larger gain. A total gain $K=K_{LPF}K_dK_oA_2$ is inversely proportional to a bandwidth of the PLL 100. An optimal bandwidth for the PLL 100 is determined for a given application. In certain examples, choosing a relatively large bandwidth (e.g., a few Hz around 1 Hz) allows improved adaptation to changes of the dominant slow-wave frequency (that can vary between 0.3 to 4 Hz). In certain examples, the PLL 100 applies a band-pass filter to isolate the time evolution around a particular frequency. In slow wave sleep applications, the natural narrow-band characteristics of the EEG are used during SWS, so the raw EEG is used as the PLL input 105.

In certain examples, the PLL 100 can also be analyzed as a control system using a Laplace transform. A closed-loop transfer function can be represented as:

$$H(s) = \frac{KF(s)}{s+KF(s)}, \quad \text{(Eq. 12)}$$

where $s=i\omega$ and $F(s)=(1+s\tau_2)/(1+s\tau_1)$ is the transfer function of the low-pass filter (e.g., a lag-lead filter, etc.).

The closed-loop transfer function can then be rewritten as:

$$H(s) = \frac{K(1+s\tau_2)}{\tau_1 s^2 + (1+K\tau_2)s + K}. \quad \text{(Eq. 13)}$$

The denominator of Equation 13 has the form of a harmonic oscillator $s^2+2\zeta\omega_n s+\omega_n^2$ where a natural frequency is $\omega_n=\sqrt{K/\tau_1}$ and a damping factor is $\zeta=\frac{1}{2}\omega_n\tau_2$. The bandwidth $\omega_h$ for the PLL 100 can be calculated then by:

$$\omega_h=\omega_n[(1+2\zeta^2+\sqrt{2+2\zeta^2}]^{1/2}. \quad \text{(Eq. 14)}$$

Another parameter that determines a relevant time scale of the PLL 100 is a lock-in time $T_L$:

$$T_L = \frac{2\pi}{\omega_n}, \quad \text{(Eq. 15)}$$

wherein TL represents a time to complete the lock-in process.

In certain examples, the PLL 100 estimates EEG phase in real time (or substantially in real time with computational delay). As soon as a certain target phase range is reached (e.g., with a bandwidth of 0.3 radians), a pulse is delivered. In rare cases, the change in the phase is so rapid that there is a jump in phase across the phase range. In that case, if more than a second is passed by the last pulse, a new tone is played to avoid big gaps between consecutive stimuli.

Certain examples tap specific resonances in the EEG to allow the brain to drive its own rhythms, corralled within a user-defined bandwidth (e.g., for delta power). The PLL provides stimulated slow waves showing characteristics typical of slow waves normally seen during natural sleep. For example, a topographical distribution of the stimulated slow waves can be nearly identical to the distribution of endogenous slow waves of stage N3 or SWS. These results confirm the viability of using automatically administered acoustic stimulation to enhance slow waves in sleep.

FIG. 2A shows a few minutes of an example EEG 210 from channel Fpz during SWS for a subject. The output 220 of the VCO 110 is also shown on the same time scale. The PLL output 135 closely follows the EEG trace 210, particularly during bursts of slow-wave activity. During times when an amplitude of the EEG is relatively small and the signal does not follow a rhythm around 1 Hz, the PLL 100 oscillates in a more regular way with a sinusoidal pattern.

The regular oscillation of the PLL 100 helps generate a tone when a certain phase range is reached for the first time. Even when a slow wave is not present, rhythmic tones are delivered in the attempt to evoke a slow wave. The tones are indicated by asterisks 230 in FIG. 2A. As shown in the example of FIG. 2A, a majority of the acoustic stimuli are delivered at the target phase that in this case is between the zero crossing and the negative peak.

Thus, while FIG. 2A shows an EEG trace for a period of slow-wave sleep 210, the VCO output for the PLL that matches the EEG trace 220, and the acoustic stimuli tones 230, FIG. 2B depicts a phase detector output 240 of the PLL 100. The PLL 100 can adapt to individual sleep patterns and characteristics without a need to be calibrated using baseline information about a subject.

Figure 3:
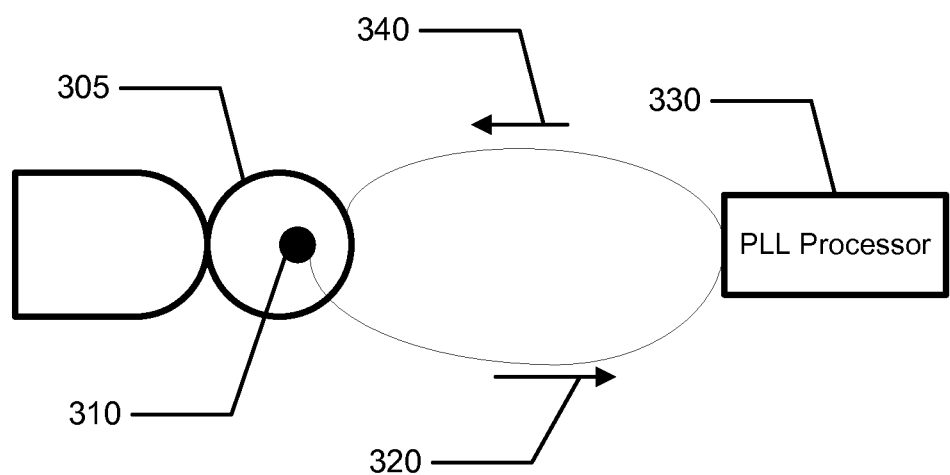
FIG. 3 depicts an example monitoring and slow wave activity stimulation configuration.

In operation, as illustrated in the example of FIG. 3, an EEG recorded from a frontal electrode 310 positioned on the head 305 of a subject during slow-wave sleep provides a PLL input 320, and a phase of the EEG is computed in real time using a PLL processor 330 to generate and deliver acoustic stimuli 340 accurately at a given phase of the EEG.

Small errors in phase-locked loops are often due either to phase jitter in the input signal or because the loop is made fast enough to follow larger phase excursions with small lag. The EEG has large phase excursions but it is not desirable to make the loop response fast, because the reference oscillator would then have a broad spectrum of its own which would distort the spectrum of the measured phase. In other words, the PLL in this application should ideally have a slow response, so that the VCO frequency remains steady at an average center frequency of the slow-wave activity.

Thus, certain examples provide a PLL generating an online estimation of slow-wave phase to facilitate regular alternation between up and down states of cortical activity during slow wave sleep. Given relevance of EEG oscillations for neural function, this technique can improve sleep-related cognitive and cardiometabolic function. For example, by stimulating slow wave activity during slow wave sleep, certain examples can improve restfulness of sleep. Certain examples can increase memory consolidation during sleep. Certain examples can increase attention and alertness during waking. Certain examples can aid in measured self-movement. Certain examples help to serve as a sleep aid, for learning and memory improvement, etc.

Figure 4:
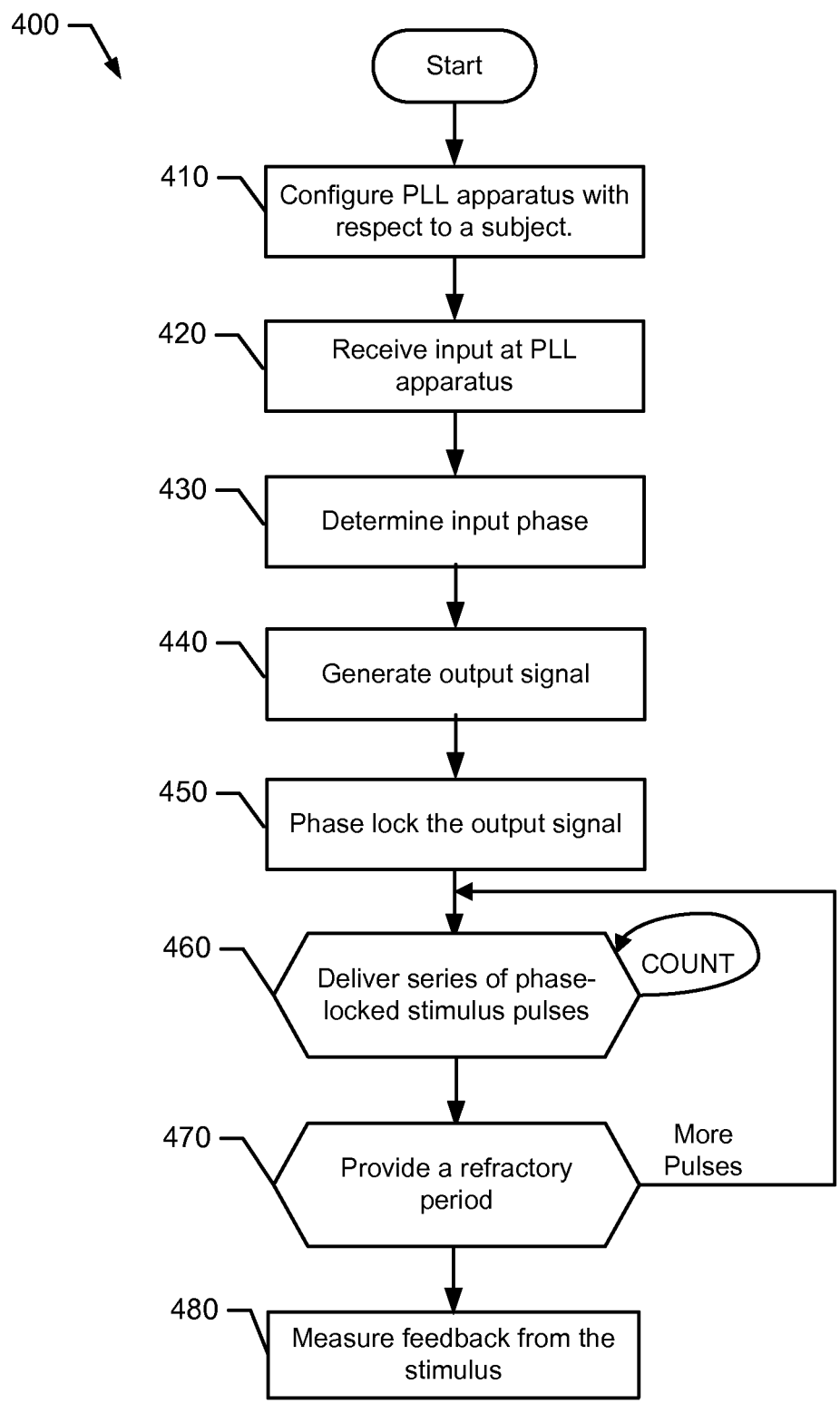
FIG. 4 illustrates a flow diagram of an example method to enhance slow wave sleep through stimulation of slow wave activity.

FIG. 4 illustrates a flow diagram of an example method 400 to enhance slow wave sleep through stimulation of slow wave activity. At block 410, a phase-lock loop (PLL) apparatus is configured with respect to a subject (e.g., a human patient). For example, electrodes and/or other transducers are provided with respect to the subject, and configuration settings are adjusted for the subject.

At block 420, an input (e.g., an EEG input) is received at the PLL apparatus. The input can include an input signal in addition to or instead of an indication of a sleep stage of the subject. For example, stimulus is desired once slow wave sleep (e.g., stages N3 and N4) is occurring. At block 430, a phase of the input signal (e.g., the EEG) is determined. For example, the phase detector 120 of the PLL can analyze and detect the phase of the input signal. At block 440, an output signal is generated based on the input signal and phase. At block 450, the output signal is phase locked according to endogenous oscillations of the brain. For example, the oscillator 110 of the PLL 100 generates a reference signal and an output signal phase-locked to the reference.

At block 460, the phase locked signal is used to deliver a stimulus in blocks of one or more pulses to the subject. For example, the stimulus is delivered in blocks of five pulses (block ON). At block 470, a refractory period is provided between blocks of pulses. For example, following a block of five pulses, a refractory period is provided in which no stimulus is applied (block OFF). The slow waves are larger in periods of stimulus (during block ON) than in refractory periods (during block OFF). Inter-mixing periods of on and off facilitate a pattern of augmented oscillation in slow waves. Thus, the PLL can efficiently track the phase of the EEG and can deliver pulses at a positive peak of the slow wave when acoustic stimulation is most beneficial in terms of physiological effects to the subject. For example, in the case of young adult subjects, the PLL can track the slow wave oscillations relatively easy given the large amplitude oscillations.

At block 480, feedback is measured from the stimulus. For example, slow wave oscillations and associated amplitude can be recorded and tracked to evaluate progress and/or other effectiveness of slow wave activity stimulation. Phase lock and/or other configuration may be adjusted based on feedback, and effects of slow wave stimulation can also be measured based on the feedback.

In an absence of major slow waves, the PLL oscillates almost sinusoidally producing regular interval tones. This sinusoidal-type oscillation is done to promote generation of slow wave activity when slow wave activity is absent or weak (e.g., as it is in the case of aging adults).

Figure 5:
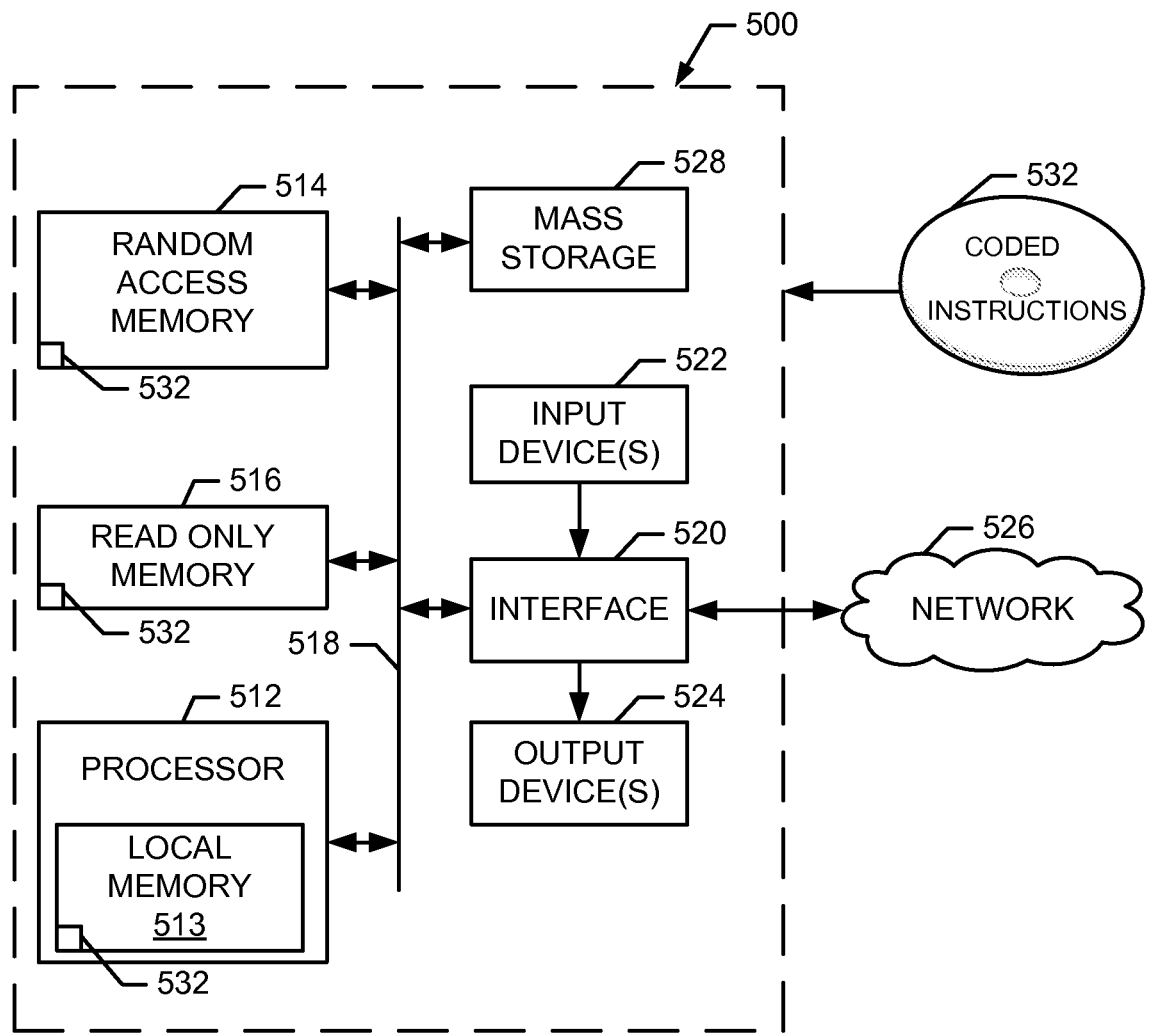
FIG. 5 is a block diagram of an example processor platform capable of executing machine readable instructions to implement systems and methods described herein.

FIG. 5 is a block diagram of an example processor platform that may be used to execute systems, methods and apparatus described herein. The processor platform 500 of the instant example includes a processor 512. For example, the processor 512 can be implemented by one or more microprocessors or controllers from any desired family or manufacturer. The processor 512 includes a local memory 513 (e.g., a cache) and is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 may be implemented by flash memory and/or any other desired type of memory device. Access to the main memory 514, 516 is controlled by a memory controller.

The processor platform 500 also includes an interface circuit 520. The interface circuit 520 may be implemented by any type of interface standard, such as an Ethernet interface, a universal serial bus (USB), and/or a PCI express interface.

One or more input devices 522 are connected to the interface circuit 520. The input device(s) 522 permit a user to enter data and commands into the processor 512. The input device(s) can be implemented by, for example, a keyboard, a mouse, a touchscreen, a track-pad, a trackball, isopoint and/or a voice recognition system.

One or more output devices 524 are also connected to the interface circuit 520. The output devices 524 can be implemented, for example, by display devices (e.g., a liquid crystal display, a cathode ray tube display (CRT), etc.). The interface circuit 520, thus, typically includes a graphics driver card.

The interface circuit 520 also includes a communication device such as a modem or network interface card to facilitate exchange of data with external computers via a network 526 (e.g., an Ethernet connection, a digital subscriber line (DSL), a telephone line, coaxial cable, a cellular telephone system, etc.).

The processor platform 500 also includes one or more mass storage devices 528 for storing software and data. Examples of such mass storage devices 528 include floppy disk drives, hard drive disks, compact disk drives and digital versatile disk (DVD) drives. The mass storage device 528 may implement a local storage device.

Coded instructions 532 (e.g., coded instructions of FIG. 4) may be stored in the mass storage device 528, in the volatile memory 514, in the non-volatile memory 516, and/or on a removable storage medium such as a CD, Blu-Ray, or DVD.

Thus, certain examples facilitate enhanced slow wave sleep. Certain examples enhance memory consolidation during sleep (e.g., by a factor of two in average in declarative memory). Certain examples help to improve sleep restfulness and alertness during waking. Certain examples provide possible metabolism and hormonal balance improvements (e.g., regulation of insulin and glucose levels).

Certain examples facilitate sound wave depolarization and repolarization to match and lock a stimulus signal to a subject's own brain waves. Stimuli can then be targeted at specific time(s) for the specific subject's brain waves and sleep pattern using a PLL. Certain examples can stimulate slow waves to improve metabolism and/or treat conditions such as hypertension, metabolic syndrome, cognitive impairment, etc. Treatment and stimulus can be tailored to the individual (e.g., particular health parameter, brain waves, patterns, etc.) and locked using a PLL. In certain examples, the PLL is an adaptive PLL which learns from brain wave feedback to adapt its code to suit the individual subject (e.g., self-adapting or self-improving).

In certain examples, the PLL can be provided in an apparatus included in a band, cap, sticker, temporary tattoo, etc., positioned on or over the subject's head. The apparatus can be connected via wired and/or wireless communication to a computer, processor, and/or other electronic circuitry to receive signals, provide commands, configure, report, and/or otherwise process signals and data, for example. In certain examples, the apparatus can be in wireless communication with a smart phone for data retrieval, processing, output, and feedback.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   identifying a sleep stage for slow wave sleep in a subject being monitored;
   generating, following identification of slow wave sleep and using a processor including a phase locked loop, an output signal including tones based on a phase of a reference input signal, the reference input signal corresponding to an electroencephalogram obtained from the subject with a phase tracked by the phase locked loop to adapt the phase locked loop to a target phase for slow wave characteristics of the subject, the output signal phase locked according to the reference input signal;
   delivering, via an interface connected to the processor and at the target phase for slow wave characteristics of the subject during slow wave sleep for the subject, an acoustic stimulus signal to the subject formed from the phase locked output signal, the delivering comprising:
   providing the stimulus signal in a series of signal pulses for a first period of time; and
   providing a refractory period without pulses in a second period of time; and
   measuring feedback from the stimulus signal;
   monitoring the phase of the reference input signal; and
   adjusting the output signal phase to keep the output signal phase matched to the reference input signal to produce the stimulus signal.

2. The method of claim 1, wherein identification of slow wave sleep comprises modeling slow wave activity over a third period of time.

3. The method of claim 1, wherein the phase locked loop comprises an electronic circuit including a phase detector and an oscillator.

4. The method of claim 3, wherein the electronic circuit compares the phase of the reference input signal with the phase of the output signal, using the phase detector, and adjusts a frequency of the oscillator to match the phase of the reference input signal with the phase of output signal in a feedback loop.

5. The method of claim 4, wherein the electronic circuit is configured to stimulate slow-wave sleep activity by rhythmically generating an acoustic tone in a given range around a target frequency and to phase lock with endogenous slow-wave oscillations of the subject's brain and deliver the stimulus signal to the brain at a particular phase based on the reference input signal and the phase locked output signal.

6. The method of claim 4, wherein, when the phase of the output signal is within a given range around the phase of the reference input signal, a first tone is output, and, when the phase of the output signal changes to exceed the reference input signal, a second tone is output.

7. The method of claim 1, wherein the reference input phase corresponds to a phase of an electrophysiological rhythm.

8. The method of claim 1, wherein the combination of the first period of time and the second period of time enables the processor to track the phase of the reference input signal and deliver the stimulus signal at a positive peak of a slow wave.

9. A non-transitory tangible machine readable medium having instructions stored thereon, which when executed, cause a machine to implement a method, the method comprising:
    identifying a sleep stage for slow wave sleep in a subject being monitored;
    generating, following identification of slow wave sleep and using a processor including a phase locked loop, an output signal including tones based on a phase of a reference input signal, the reference input signal corresponding to an electroencephalogram obtained from the subject with a phase tracked by the phase locked loop to adapt the phase locked loop to a target phase for slow wave characteristics of the subject, the output signal phase locked according to the reference input signal;
    delivering, via an interface connected to the processor and at the target phase for slow wave characteristics of the subject during slow wave sleep for the subject, an acoustic stimulus signal to the subject formed from the phase locked output signal, the delivering comprising:
        providing the stimulus signal in a series of signal pulses for a first period of time; and
        providing a refractory period without pulses in a second period of time;
    measuring feedback from the stimulus signal;
    monitoring the phase of the reference input signal; and
    adjusting the output signal phase to keep the output signal phase matched to the reference input signal to produce the stimulus signal.

10. The machine readable medium of claim 9, wherein identification of slow wave sleep comprises modeling slow wave activity over a third period of time.

11. The machine readable medium of claim 9, wherein the phase locked loop comprises an electronic circuit including a phase detector and an oscillator.

12. The machine readable medium of claim 11, wherein the electronic circuit compares the phase of the reference input signal with the phase of the output signal, using the phase detector, and adjusts a frequency of the oscillator to match the phase of the reference input signal with the phase of output signal in a feedback loop.

13. The machine readable medium of claim 12, wherein the electronic circuit is configured to stimulate slow-wave sleep activity by rhythmically generating an acoustic tone in a given range around a target frequency and to phase lock with endogenous slow-wave oscillations of the subject's brain and deliver the stimulus signal to the brain at a particular phase based on the reference input signal and the phase locked output signal.

14. The machine readable medium of claim 12, wherein, when the phase of the output signal is within a given range around the phase of the reference input signal, a first tone is output, and, when the phase of the output signal changes to exceed the reference input signal, a second tone is output.

15. The machine readable medium of claim 9, wherein the reference input phase corresponds to a phase of an electrophysiological rhythm.

16. A system comprising:
    a memory and processor including a phase locked loop, the memory storing instructions which, when executed by the processor, cause the processor to:
    identify a sleep stage for slow wave sleep in a subject being monitored;
    generate, following identification of slow wave sleep, an output signal based on a phase of a reference input signal, the reference input signal corresponding to an electroencephalogram obtained from the subject with a phase tracked by the phase locked loop to adapt the phase locked loop to a target phase for slow wave characteristics of the subject, the output signal phase locked according to the reference input signal;
    deliver, via an interface connected to the processor and at the target phase for slow wave characteristics of the subject during slow wave sleep for the subject, an acoustic stimulus signal to the subject formed from the phase locked output signal, the delivering comprising:
        providing the stimulus signal in a series of signal pulses for a first period of time; and
        providing a refractory period without pulses in a second period of time;
    measure feedback from the stimulus signal;
    monitoring the phase of the reference input signal; and
    adjusting the output signal phase to keep the output signal phase matched to the reference input signal to produce the stimulus signal.

17. The system of claim 16, wherein identification of slow wave sleep comprises modeling slow wave activity over a third period of time.

18. The system of claim 16, wherein the phase locked loop comprises an electronic circuit including a phase detector and an oscillator.

19. The system of claim 18, wherein the electronic circuit compares the phase of the reference input signal with the phase of the output signal, using the phase detector, and adjusts a frequency of the oscillator to match the phase of the reference input signal with the phase of output signal in a feedback loop.

20. The system of claim 19, wherein the electronic circuit is configured to stimulate slow-wave sleep activity by rhythmically generating an acoustic tone in a given range around a target frequency and to phase lock with endogenous slow-wave oscillations of the subject's brain and deliver the stimulus signal to the brain at a particular phase based on the reference input signal and the phase locked output signal.

21. The system of claim 19, wherein, when the phase of the output signal is within a given range around the phase of the reference input signal, a first tone is output, and, when the phase of the output signal changes to exceed the reference input signal, a second tone is output.

22. The system of claim 16, wherein the combination of the first period of time and the second period of time enables the processor to track the phase of the reference input signal and deliver the stimulus signal at a positive peak of a slow wave.

* * * * *